United States Patent [19]
Higo et al.

[11] Patent Number: 5,908,400
[45] Date of Patent: Jun. 1, 1999

[54] DEVICE STRUCTURE FOR IONTOPHORESIS

[75] Inventors: Naruhito Higo; Hirotoshi Adachi; Tatsuya Meno, all of Tsukuba, Japan

[73] Assignee: Hisamitsu Pharmaceutical Co., Inc., Tosu, Japan

[21] Appl. No.: 08/878,852

[22] Filed: Jun. 20, 1997

[30] Foreign Application Priority Data

Jun. 20, 1996 [JP] Japan .................................. 8-181481

[51] Int. Cl.$^6$ .................................................. A61N 1/30
[52] U.S. Cl. ............................................................ 604/20
[58] Field of Search .............................. 604/20; 607/115, 607/145, 152, 153

[56] References Cited

U.S. PATENT DOCUMENTS

| | | | |
|---|---|---|---|
| 3,853,837 | 12/1974 | Fujino et al. ........................ | 260/112.5 |
| 3,972,859 | 8/1976 | Fujino et al. ........................ | 260/112.5 |
| 4,008,209 | 2/1977 | Fujino et al. ........................ | 260/112.5 |

(List continued on next page.)

FOREIGN PATENT DOCUMENTS

| | | |
|---|---|---|
| 0 031 567 | 7/1981 | European Pat. Off. . |
| 0 357 061 | 3/1990 | European Pat. Off. . |
| 0 359 036 | 3/1990 | European Pat. Off. . |

(List continued on next page.)

OTHER PUBLICATIONS

Pharmazie 49, (1994) H. 7 pp. 538–539.
Advanced Drug Delivery Reviews, vol. 9, pp. 119–135 (1992) What are the pathways of iontophoretic current flow through mammalian skin?.
Endocrinology, vol. 93, pp. 1349–1353 (1973) Bovine Parathyroid Hormone: Minimum Chain Length of Synthetic Peptide Required for Biological Activity.
Endocrinology, vol. 131, No. 6, pp. 2885–2890 (1992) A Chimeric Analog of Human and Salmon Calcitonin Eliminates Antigenicity and Reduces Gastrointestinal Disturbances.
Journal of Clinical Experimental Medicine vol. 125, No. 10, pp. 835–843 (1983).
Journal of Controlled Release, vol. 18, pp. 213–220 (1992) In vivo transdermal iontophoretic delivery of growth hormone releasing factor GRF (1–44) in hairless guinea pigs.
Journal of Society of Endocrinology, Japan vol. 54, No. 5, pp. 676–691 (1978).
Pharmaceutical Research, vol. 3, No. 6, pp. 318–326 (1986) Iontophoretic Devices for Drug Delivery.
Proceedings of the National Academy of Science, vol. 78, No. 10 pp. 6509–6512 (1981) Inhibition of prostate tumor growth in two rat models by chronic administration of D–Trp$^6$ analogue . . . .
Science, vol. 221, pp. 719–725 (1983) Angiogenesis Inhibition and Tumor Regression Caused by Heparin or a Heparin Fragment in the Presence of Cortisone.

*Primary Examiner*—Corrine M. McDermott
*Assistant Examiner*—Sharon Finkel
*Attorney, Agent, or Firm*—Flynn, Thiel, Boutell & Tanis, P.C.

[57] ABSTRACT

An iontophoretic device structure of the dissolution-on-use type is provided, wherein an ionized drug is transdermally or transmucosally administered into a living body. The device structure comprises (a) a non-polarizable electrode, (b) a hydrophilic, polymeric gel layer containing an ion exchange resin which is able to specifically inhibit the movement of ions dissolved out from the electrode while in use, and (c) a drug layer containing a drug in a dry condition in a drug retaining membrane, wherein when said device is in use, said drug layer is brought into contact with said hydrophilic, polymeric gel layer so that said drug in the dry condition is dissolved. A humectant may be contained in the hydrophilic, polymeric gel layer and/or the drug layer.

29 Claims, 4 Drawing Sheets

U.S. PATENT DOCUMENTS

| | | | |
|---|---|---|---|
| 4,086,219 | 4/1978 | Wittle et al. | 260/112.5 |
| 4,087,390 | 5/1978 | Shields | 260/8 |
| 4,093,574 | 6/1978 | Shields | 260/8 |
| 4,100,117 | 7/1978 | Shields | 260/8 |
| 4,124,577 | 11/1978 | Tinney et al. | 260/112.5 |
| 4,229,438 | 10/1980 | Fujino et al. | 424/177 |
| 4,253,997 | 3/1981 | Sarantakis | 260/8 |
| 4,253,998 | 3/1981 | Sarantakis | 260/8 |
| 4,277,394 | 7/1981 | Fujino et al. | 260/112.5 |
| 4,317,815 | 3/1982 | Coy et al. | 424/177 |
| 4,474,570 | 10/1984 | Ariura et al. | 604/20 |
| 4,764,164 | 8/1988 | Sasaki | 604/20 |
| 4,927,408 | 5/1990 | Haak et al. | 604/20 |
| 5,080,646 | 1/1992 | Theeuwes et al. | 604/20 |
| 5,135,480 | 8/1992 | Bannon et al. | 604/20 |
| 5,158,537 | 10/1992 | Haak et al. | 604/20 |
| 5,162,042 | 11/1992 | Gyory et al. | 604/20 |
| 5,169,383 | 12/1992 | Gyory et al. | 604/20 |
| 5,250,022 | 10/1993 | Chien et al. | 604/20 |
| 5,362,308 | 11/1994 | Chien et al. | 604/20 |
| 5,503,632 | 4/1996 | Haak | 604/20 |
| 5,788,666 | 8/1998 | Atanasoska | 604/20 |

FOREIGN PATENT DOCUMENTS

| | | |
|---|---|---|
| 0 386 667 | 9/1990 | European Pat. Off. |
| 0 411 146 A1 | 2/1991 | European Pat. Off. |
| 0 415 294 | 3/1991 | European Pat. Off. |
| 0 477 885 | 4/1992 | European Pat. Off. |
| 0 510 662 | 10/1992 | European Pat. Off. |
| 0 643 981 A1 | 3/1995 | European Pat. Off. |
| 0 747 092 A2 | 12/1996 | European Pat. Off. |
| 50-121273 | 9/1975 | Japan. |
| 52-116465 | 9/1977 | Japan. |
| 61-259679 | 11/1986 | Japan. |
| 62-99333 | 5/1987 | Japan. |
| 62-126138 | 6/1987 | Japan. |
| 62-135435 | 6/1987 | Japan. |
| 63-102768 | 5/1988 | Japan. |
| 63-502404 | 9/1988 | Japan. |
| 4-247034 | 9/1992 | Japan. |
| 5-32696 | 2/1993 | Japan. |
| 5-339170 | 12/1993 | Japan. |
| 1 423 083 | 1/1976 | United Kingdom. |
| WO 92/00753 | 1/1992 | WIPO. |
| WO 93/10163 | 5/1993 | WIPO. |
| WO 93/24177 | 12/1993 | WIPO. |
| WO 93/25168 | 12/1993 | WIPO. |

DEVICE STRUCTURE FOR IONTOPHORESIS

BACKGROUND OF THE INVENTION

1. Field of the Invention

This invention relates to an iontophoretic device structure of the dissolution-on-use type which is useful for transdermal or transmucosal delivery of drugs or biologically active substances into living bodies in the medical field. It is to be noted that the term "drugs and biologically active substance" used herein may be sometimes referred to simply as "drugs".

2. Prior Art

Iontophoresis is a system of promoting transdermal or transmucosal absorption by the use of electricity as an external stimulation. In the system, the transmittance of the molecules of a drug or medicine through a skin barrier is promoted on the basis of the principle that, in the electric field produced between the anode and the cathode by application of an electric current, positively charged molecules of the drug are moved from the anode toward the cathode and negatively charged molecules are moved from the cathode toward the anode [Journal of Controlled Release, Vol. 18, 213–220 (1992), Advanced Drug Delivery Review, Vol. 9, 119 (1992), and Pharmaceutical Research, Vol. 3, 318–326 (1986)].

Recent advances of synthetic technologies and genetic engineering lead to pure and mass production of naturally-occurring peptides or proteins, those peptides or proteins wherein their amino acid compositions are changed, or chemically modified derivatives thereof. The applications of these substances as drugs have now been expected. On the other hand, however, as studies on these peptides or proteins are in progress, it has been made clear that the diversity of biological activities of the peptides or proteins are physiologically controlled by the minute and complicated in vivo kinetics. In order to permit a peptide or protein to show the maximum medical efficacy on a specific disease and to suppress its side effect to a minimum, there has been required a system which enables one to strictly control the dosage of the peptide or protein. For instance, calcitonin has the capability of keeping the amount of bone from being reduced by suppression of the absorption of bone and is thus employed for the treatment of osteoporosis or Paget's disease. However, an excessive administration brings about a side effect such as inappetence. In addition, for the improvement of the treating effect, it is essential to repeatedly administer the peptide or protein.

It is known that some types of peptides develop different medical efficacies depending on the manner of administration thereof. For instance, parathormone exhibits different actions which are contrary to each other, i.e. a bone absorption-promoting action and bone formation-promoting action. When intravenously injected at a given rate, this hormone develops the bone resorption-promoting action, whereas the bone formation-promoting action is strongly developed by frequent administration through subcutaneous injection. In order to employ the parathormone as a drug for treating osteoporosis while expecting its bone formation-promoting action, the preparation thereof has to be of the pulse-release type, not of the slow release type. However, it is known that such a biologically active peptide or protein is usually decomposed in a digestive fluid in the gastrointestinal tract, or is hydrolyzed with a hydrolase present in the digestive tract walls, and thus is poor in an absorption efficiency. This means that any satisfactory medical efficacy cannot be expected when these biologically active peptides or proteins are orally administered. Thus, the usual practice is to administer them through injection. However, an injection causes a great pain to a patient, and is hence unsuitable for self administration, thus imposing a great burden on the patient. This will become so much the worse for the case where repeated, continuous administration is required, for example, as in the case of the afore-indicated calcitonin or parathormone.

In the pharmaceutical or medical field, attention has now been paid to iontophoresis which is a novel drug delivery system responsible for the administration of such biologically active peptides or proteins, and extensive studies have been made thereon. More particularly, if drugs which have conventionally been able to be administered only as an injection can be self-administered by a patient himself according to the iontophoresis, this will clear the way for treatment at home. The precise control in time of application of an electric current permits a desired absorption pattern to be created. Especially, in the supplemental therapy of an endogenous compound, it is conceivable to realize more effective therapy with the compound while taking the circadian rhythm of a living body into account.

On the other hand, extensive studies have been made on the devices to be employed for the iontophoresis so as to have drugs transdermally absorbed in an efficient manner. The device has a fundamental structure which includes a layer containing an electrolyte, and a layer comprised of at least a partially ionized drug. A porous membrane such as a non-woven fabric is used, for example, as the drug layer. During use, a potential is applied via an electrode which has been preliminarily disposed in the electrolyte layer or on the upper surface thereof, so that the drug is delivered to a living body from the surface such as of the porous membrane via the skin.

However, such devices have a number of defects to be overcome. For instance, Japanese Laid-open Patent Application No. 63-502404 sets out a device which includes a cavity containing an electrolyte, another cavity containing at least a partially ionized drug, and an ion exchange membrane provided between the cavities and capable of suppressing the movement of competitive ions produced from electrodes. In U.S. Pat. Nos. 5,250,022 and 5,362,308, there are proposed devices which include a housing provided with a first chamber accommodating an electrolyte therein and a second chamber accommodating an ionized drug, wherein the first chamber comprises an ion exchange resin for suppressing the movement of competitive ions produced from electrodes and also a semi-permeable membrane for preventing the drug from being reversely diffused.

However, these devices commonly have the problem that when dried, the ion exchange membrane cracks, with the great possibility that the ion selectivity lowers considerably. Avoiding the problem leads to the disadvantage that the steps of fabricating the devices become more complicated. In both United States Patents, the ion exchange resin and the semi-permeable membrane are employed in the first chamber. Where the semi-permeable membrane and the first chamber portion are poorly bonded, there is the apprehension that the drug is reversely diffused through the gap formed between the membrane and the first chamber portion. Moreover, as having set out hereinabove, these devices essentially require an additional ion exchange membrane, or the provision of an ion exchange resin and a semi-permeable membrane, with their structures becoming complicated.

On the other hand, where a drug contained in devices is in the form of a solution and is thus unstable and, especially, where the drug consists of a biologically active peptide or protein, it undergoes a non-reversible change, such as hydrolysis, association or coagulation, in the solution. This results in the lowering of activity during storage or prior to the use of the device. In order to overcome this problem, it is convenient to use a device of the dissolution-on-use type wherein a drug is preserved or kept in a dry condition. For instance, WO93224177 sets forth a device of the type which comprises a reserver layer containing an electrode and a drug, both in a dried condition, and a water supplying layer disposed above the reserver layer wherein when a tab provided between both layers is removed, the drug is dissolved. Moreover, Japanese Laid-open Patent Application No. 63-102768 sets out a device wherein capsules for water supplement are incorporated into an electrode and a drug layer in a dry condition.

However, these devices have such a special structure capable of holding the liquid compartment that the device structure becomes complicated as a whole. In addition, when using an ion exchange membrane having an ion selective function or a combination with an ion exchange resin, the resultant device becomes more complicated in structure. Hence, the fabrication of these devices requires correspondingly a greater number of steps, presenting the problem that the fabrication costs become very high.

Aside from the above-stated problems involved in the hitherto known iontophoretic devices, we found through observation of this type of device having been actually made by us that prior to the use of the device, the reverse diffusion of a drug and the ionization of an electrode-constituting metal were observed. Not only the reverse diffusion and the ionization impeded the performance of the device on use, but also the metal ions arrived at a skin at an early stage where they were absorbed in the living body, thereby causing damages thereto. Additionally, it was also found that as the dissolved-out metal ions moved, they served to impede the movement of a drug to be delivered from the device and the transdermal absorption thereof.

In order to solve the problems of the prior art iontophoretic devices, we made intensive studies and investigations on this type of device. As a result, it was found that when the device is arranged to be of the dissolution-on-use type wherein a hydrophilic, polymeric gel layer dispersing an ion exchange resin therein is provided between a non-polarizable electrode and a drug layer, metal ions can be specifically prevented from being dissolved out from the non-polarizable electrode, and the reverse diffusion of a drug prior to the use of the device can be appropriately prevented. By this, the device ensures the long-term capability of an electric current being applied thereto so that the drug can be reproducibly, transdermally administered at high bioavailability. The invention has been accomplished based on the above findings.

SUMMARY OF THE INVENTION

It is accordingly an object of the invention to provide a device structure for iontophoresis wherein when a drug which is unstable in the form of a solution is administered through iontophoretic, the device ensures increased stability of such a drug when preserved.

It is another object of the invention to provide a device structure for iontophoresis which can specifically prevent the movement of metal ions dissolved out from a non-polarizable electrode and which can prevent reverse diffusion of a drug prior to the use thereof.

It is a further object of the invention to provide a device structure for iontophoresis which ensures the long-term capability of being applied with an electric current without lowering the transport number of a drug to be used and can completely prevent or suppress deposition of an electrode component on the skin, thereby permitting the drug to have a high bioavailability.

According to one embodiment of the invention, there is provided an iontophoretic device structure of the dissolution-on-use type wherein an ionized drug is transdermally or transmucosally administered into a living body, the device structure comprising (a) a non-polarizable electrode, (b) a hydrophilic, polymeric gel layer dispersing an ion exchange resin capable of specifically inhibiting the movement of ions dissolved out from the electrode during use of the device, and (c) a layer of a drug kept in a dry condition wherein when the device is in operation, the layer of the drug is brought into contact with the hydrophilic, polymeric gel layer so that the drug kept in the dry condition is dissolved.

According to another embodiment of the invention, there is also provided an iontophoretic device structure of the dissolution-on-use type wherein an ionized drug is transdermally or transmucosally administered into a living body, the device structure comprising (a) a non-polarizable electrode, (b) a hydrophilic, polymeric gel layer dispersing an ion exchange resin capable of specifically inhibiting the movement of ions dissolved out from the electrode during use of the device, (c) a drug layer wherein a drug is held in a drug retainer in a dry condition, and (d) a humectant incorporated in either or both of the hydrophilic, polymeric gel layer and the drug retainer, wherein when the device is in operation, the drug layer is brought into contact with the hydrophilic, polymeric gel layer so that the drug kept in the dry condition is dissolved. It should be noted that the iontophoretic device of the invention is usually applied to a skin and may, of course, be applied to mucosae.

DETAILED DESCRIPTION OF THE INVENTION

The non-polarizable electrode used in the device of the invention may be used as either an anode or a cathode and should preferably be used as an anode. Where the non-polarizable electrode is used as an anode, it is preferred that the electrode is constituted of silver or a mixture containing silver. The hydrophilic, polymeric gel layer is made of polysaccharides, their derivatives or salts thereof. The ion exchange resin contained in the hydrophilic, polymeric gel layer may be made of either a cation exchange resin or an anion exchange resin. Preferably, anion exchange resins are used. Preferred examples of the anion exchange resin include those anion exchange resins containing a quaternary ammonium group as a functional group and a chloride ion. The drug layer should preferably comprise a member having a porous or capillary structure. The drugs to be ionized include various types of drugs which are ionizable and have the capability of transdermal absorption, e.g. biologically active peptides or proteins having a molecular weight of about 8000 or below or low molecular weight drugs. Examples of the biologically active peptides include calcium-controlling hormones, typical of which are those calcium-controlling hormones selected from parathormone, its derivatives and salts thereof.

In the practice of the invention, it is preferred that a humectant is contained in the hydrophilic, polymeric gel layer and/or the drug layer. When using a humectant, evaporation of water or moisture from a drug solution at the time of administration of the drug can be suppressed, ensuring good passage of an electric current over a long time. The humectant acts on keratin, which serves as a barrier for the skin permeation of the drug, so that the transdermal or transmucosal absorption of the drug is promoted in response to an electric current being applied (in such a way that the drug is absorbed only at the time of application of the electric current, not at the time when any electric current is not passed). In this manner, the drug can be utilized at a high bioavailability. Although the humectant will be hereinafter described in detail, the mixtures of urea and L-proline are preferably used. The term "the humectant contained in the hydrophilic, polymeric gel layer and/or the drug layer" used herein means three cases: a case where the humectant is contained only in the hydrophilic, polymeric gel layer; a case where the humectant is contained in the drug layer; and a case where the humectant is contained in the hydrophilic, polymeric gel layer and the drug layer. Whenever the term "A and/or B" is used in this specification, this means (1) A alone and (2) B alone (i.e. whichever A or B), and both A and B, i.e. all the cases (1), (2) and (3).

Figure 1:
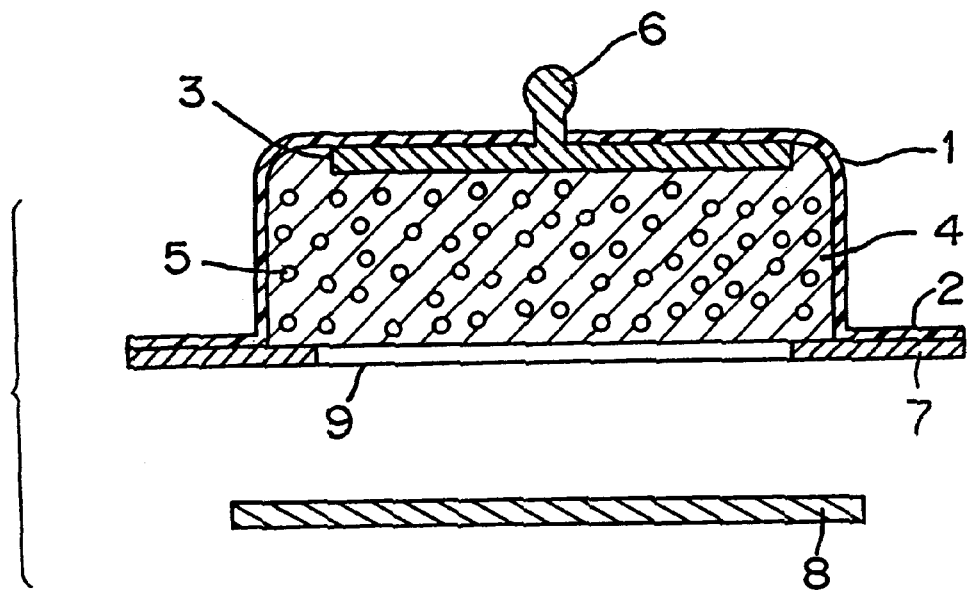
FIG. 1 is a schematic sectional view showing a device prior to its use according to an embodiment of the invention.
Figure 2:
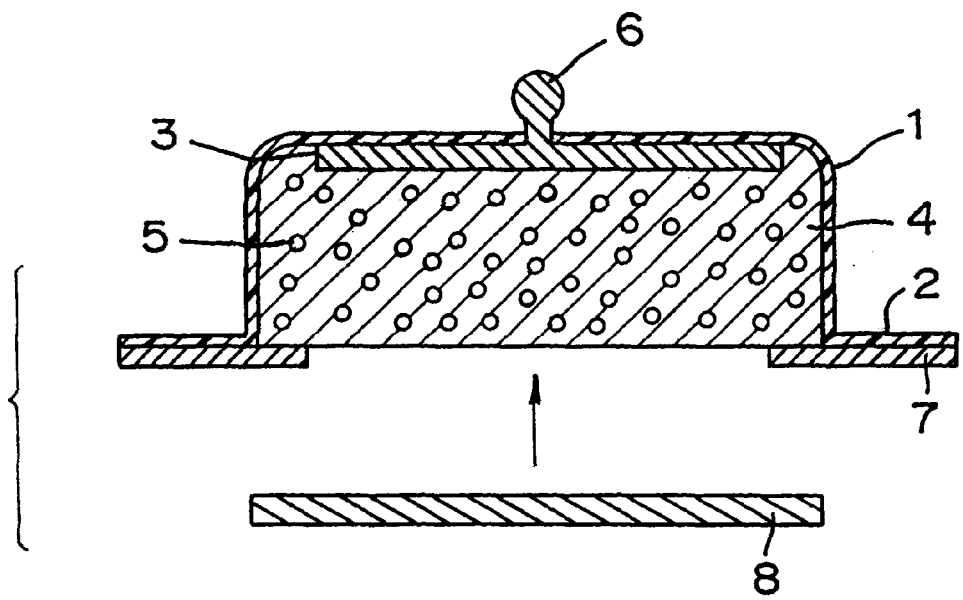
FIG. 2 is a schematic sectional view showing the device of FIG. 1 just before the use thereof.

Reference is now made to the accompanying drawings and particularly to FIGS. 1 and 2. FIG. 1 is a schematic sectional view showing an iontophoretic device structure of the dissolution-on-use type prior to its use according to an embodiment of the invention. FIG. 2 is likewise a schematic sectional view of the device just before the use. In FIG. 1 and 2, there is shown a cup-shaped container 1 having a cylindrically recessed portion. The container 1 has an extension 2 around a peripheral portion of a lower end thereof. The extension 2 is integrally constituted of the body of the container 1 as shown in the figures, but may be separately constituted of the body of the container 1 and fixedly disposed at the lower end periphery of the container 1. Reference numeral 3 indicates an electrode, reference numeral 4 indicates a hydrophilic, polymeric gel layer, and reference numeral 5 indicates an ion exchange resin. As shown, the ion exchange resin in the form of particles is dispersed in and/or mixed with the hydrophilic, polymeric gel layer 4. The electrode 3 is attached to a connection terminal 6 (i.e. a connector to an electric source) which is exposed through a small hole made at the central portion of the cup-shaped container 1 as shown. A self-adhesive layer 7 is fixedly provided at the lower surface of the extension 2 around the lower end periphery of the container 1. When used, the device is attached to and fixed on a skin through the self-adhesive layer 7. It will be noted here that the self-adhesive layer is much thinner than other members and such a thin layer is sufficient for the purpose, but is depicted as relatively thick in the figures. In FIG. 1, reference numeral 9 indicates a water and moisture-impermeable liner. Evaporation of moisture prior to use can be prevented by means of the liner 9. Reference numeral 8 indicates a drug-retaining membrane or drug retainer. In practice, the drug-retaining membrane is in contact with a skin.

In the embodiment of FIGS. 1 and 2, the cup-shaped container is shaped as being circular in section. The sectional configuration may be in the form of polygons such as a triangle, a rectangle, a pentagon and the like, an ellipse, an irregular curve and the like. In this case, the hydrophilic, polymeric gel layer 4 and the drug-retaining membrane 8 should be formed in conformity with a selected sectional configuration of the cup-shaped container, respectively. The extension 2 provided along the lower end periphery of the cup-shaped container 1 is so designed that its lower face is at the same level or substantially as the same level as the lower face of the hydrophilic, polymeric gel layer 4. Further, although the cup-shaped container 1 is depicted in the form of a cup in the embodiment of FIGS. 1 and 2, its thickness may be appropriately determined depending on the required thickness of the gel layer 4 placed in the recessed portion of the container 1. For instance, a dish-shaped container may be used.

The container 1, the electrode 3 and the self-adhesive layer 7 may be made of materials which are sufficient to play required roles as the respective members.

More particularly, the cup-shaped container 1 may be constituted, for example, of polypropylene with its inner diameter of about 30 mm. The electrode 3 is made, for example, of a silver foil punched in the form of a circle having a diameter of about 25 mm and a thickness of about 0.04 mm and disposed at the bottom of the container. The hydrophilic, polymeric gel layer 4 may consist, for example, of an agar layer (commercially available, for example, from Ina Foods Co., Ltd. under the designation of UP-16). In the hydrophilic, polymeric gel layer 4, the ion exchange resin 5 containing 8 wt % of cholestyramine resin (strongly basic anion exchange resin) is mixed. The self-adhesive layer 7 may be constituted, for example, of a self-adhesive sheet having an opening whose diameter is about 23 mm (e.g. Blenderm (trademark), Registered Trade Name of 3M Pharmaceuticals M.N.). Although, in the embodiment shown in FIG. 1, the diameter of the self-adhesive layer 7 is illustrated as being smaller than the inner diameter of the cup-shaped container 1, both diameters may be appropriately chosen as desired.

The drug-retaining membrane 8 is attached to the self-adhesive layer 7 at the peripheral portion thereof and, thus, has a size greater than the diameter of about 23 mm for the opening of the self-adhesive layer 7. For instance, the membrane 8 is so arranged as to have a diameter of about 28 mm with its thickness of about 0.125 mm. The drug-retaining membrane 8 may be made, for example, of Durapore (Registered Trade Name of Millipore Co., Ltd.). A drug has been preliminarily retained in the membrane. When used, the membrane is brought into contact with a skin. Where a humectant or wetting component, or a component consisting of a humectant and a buffer solution is used in order to suppress the evaporation of water from a drug solution and to ensure a good passage of an electric current over a long time, the component is formulated in the hydrophilic, polymeric gel layer 4 and/or the drug-retaining membrane 8. In FIG. 2, the arrow (↑) indicates the direction of contact and attachment of the drug-retaining membrane 8 to the self-adhesive layer 7. Just prior to the use of the device, the liner 9 illustrated in FIG. 1 is removed, after which the drug-retaining membrane 8 is contacted and attached to the self-adhesive layer 7 on one side thereof, followed by contact of the opposite side of the membrane 8 to a portion to be applied such as a skin.

The transdermal administration of a drug through iontophoresis can be carried out by applying a DC voltage between the electrode of the device and a reference electrode. A power supply may be one which is able to apply a continuous DC voltage or a pulse DC voltage. Of these, a power supply capable of applying a pulse DC voltage is preferred. The power supply for the pulse DC voltage should preferably be one which is able to apply a square pulse DC voltage. The frequency of the pulse DC voltage should preferably be selected from a range of from 0.1 to 200 kHz, more preferably from 1 to 100 kHz, and most preferably from 5 to 80 kHz. The on/off ratio of the pulse DC voltage is selected from a range of from 1/100 to 20/1, preferably from 1/50 to 15/1 and more preferably from 1/30 to 10/1. The application time for continuous application is 24 hours or below, preferably 12 hours or below, and more preferably 6 hours or below. For intermittent application, the application time is 24 hours or below, preferably 12 hours or below and more preferably 6 hours or below, each in total time.

The invention is described in more detail. It should be noted that where amino acids, peptides and the like are expressed in terms of abbreviations in the present specification, the abbreviations used are those defined according to IUPAC-IUB Commission on Biochemical Nomenclature or those based on conventionally employed abbreviations. If there are optical isomers for amino acids, an amino acid used means an L isomer unless otherwise indicated.

The iontophoretic device structure of the invention is of the dissolution-on-use type which has a non-polarizable electrode and a hydrophilic, polymeric gel layer formed in contact with the electrode and containing an ion exchange resin, wherein when used as a device, a drug layer containing an effective component in a dry condition is brought into contact with the hydrophilic, polymeric gel layer so that the drug in the layer is dissolved. The manner of reinforcing the structure, i.e. a packing composition or structure, is not critical.

The non-polarizable electrode used in the practice of the invention should be one which is substantially free of any generation of an oxygen gas or the like at an anode or a hydrogen gas at a cathode on application of an electric current when placed in an ordinarily employed solution composition and which undergoes no pH change as will be caused by the gas generation. The electrode material includes, for example, silver, aluminium, zinc, copper or iron. Of these, silver has good electric characteristics such as a resistance. When a silver paste is used to make the electrode, it can be fabricated efficiently and inexpensively. So far as the electrode is limited to a cathode, all metallic materials may be usable provided that they do not undergo any corrosion during storage. When using this type of non-polarizable electrode, the solution undergoes no pH change and the electrode is safe with regard to skin irritation.

The ion exchange resin for the anode used in the present invention may be one which can completely inhibit or impede the movement of metal ions dissolved out from the non-polarizable electrode and which does not attach to a skin. The ion exchange resins having such properties as mentioned above include chelate resins which are able to inhibit or impede the movement of metal ions by the chelating action thereof. Examples of the chelate resin include Amberlite IRC-718, IRA-743 (Organo Co., Ltd.), Diaion CR-10, CR-20 and CRB-02 (Mitsubishi Kasei Corporation), Dowex A-1 (Dow Chemical Co.), Duolite C-467, CS-346 (Rohm & Haas Co.), and Lewatit TP-207, TP-214, OC-1060 (Bayer AG.).

The ion exchange resins used in the present invention may be cation exchange resins which utilize the exchange reaction with the metal ions dissolved out from the electrode. Examples of such a resin include Amberlite XT-1004, IR-120B, IR-122, IR-124, 252, XT-1031, 200C, IRC50, IRC-76 (Organo Co., Ltd.), Diaion SK-1B, SK-104, SK-110, PK-208, PK-216, WK-10, WK-11, WK-20 (Mitsubishi Kasei Corp.), Dowex HCR-S, HGR-W2, 88, MWC-1H (Dow Chemical Co.), Duolite C-20, C-26, C-264, C-3, C-433, C-464 (Rohm & Haas Co.), Imac C-12, C-16P, Z-5, GT-73, Lewatit S-100, SP-112, SP-120, S-109, CNP-80 (Bayer AG.), and inorganic ion exchangers such as Bio-Rad, ZP-1, ZM-1, ZT-1, AMP, KCF-1, HZO-1, HTO-1 (Bio-Rad Co.), AMD-Erba, HMD-Erba, HAP-Erba, ZPH-Erba, TDO-Erba, Cox-Erba, AAO-Erba, CUC-Erba, CUS-Erba (Carlo Erba Co.). Zerwat, Allasion Z (Dia Prosim Co.), Ionac C100, C101, C102, M-50 (Ionac. Chem. Comp. Co.), Decalsco (F,Y), Zeo-Dur, Zerolite Green Sand (Permit Co.), and IXE-300, IXE-400, IXE-100, IXE-500, IXE-1000 (Toa Gosei Industry Co., Ltd.).

Likewise, the ion exchange resins used in the present invention may be anion exchange resins which make use of the chemical reaction with the ions from the electrode. Examples of the resin include Amberlite IRA-400, IRA-401, IRA-402, IRA-420, XT-5007, IRA-900, IRA-904, IRA-938, IRA-458, IRA-958, IRA-410, IRA-411, IRA-416, IRA-910, IRA-68, IRA-35 (Organo Co., Ltd.),Diaion SA-10A, SA-11A, SA-12A, PA-306, PA-312, PA-318, SA-20A, SA-21A, PA-406, PA-412, PA-418 (Mitsubishi Kasei Corporation), Dowex SBR, SBR-P, 11, MSA,-1, SAR, MSA-2, 66, WGR-2 (Dow Chemical Co.), Duolite A-113 plus, A-147, A-161, A-132, A-116 plus, A-162, A-368, A-7 (Rhom & Haas Co.), Imac A-34, A-33, A-31, A-32, A-205, A-28, Lewatit M-500, MP-500, AP-247A, M-600, MP-600, MP-62, OC-1059, CA-9222 (Bayer AG.), and cholestyramine. In the practice of the invention, any of these compounds mentioned above may be usable, of which anion exchange resins are preferably used. More preferably, anion exchange resins which consist of quaternary ammonium salts containing a chloride ion are used. Although styrene, acrylic and methacrylic resins are ordinarily used as a polymer backbone, any polymer backbones for ion exchange resin may be used without limitation to the above-mentioned ones. The resins may be either of the soluble type or of the sparingly soluble type unless they adversely influence functionality.

For instance, when using an electrode containing a divalent metal ion ($X^{2+}$) as an anode, an iminodiacetic acid-type resin as a chelate resin, and water as a solvent, the reaction in the reaction layer can be shown by the formula (A) indicated below $$R-N(CH_2COOH)_2 + X^{2+} \rightarrow R-N(CH_2COO)_2^{2-} X^{2+} + 2H^+ \qquad (A)$$

As will be apparent from the above, the ions dissolved out from the electrode are captured in the resin layer, thereby suppressing migration to a skin. Other resins of this type include polyamine-type resins, phosphoric acidtype resins, aminophosphoric acid-type resins, thiol-type resins, dithiocarbamic acid-type resins, amidoxime-type resins, and glucamine-type resins.

In another instance using an electrode containing a monovalent metal ion ($X^+$) as an anode, a sulfonate-type resin as a cation exchange resin (where a counter ion is a sodium ion), and water as a solvent, the reaction in the resin is shown according to the following formula (B)

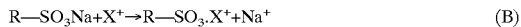

$$R-SO_3Na + X^+ \rightarrow R-SO_3.X^+ + Na^+ \quad\quad (B)$$

Thus, the ion ($X^+$) dissolved out from the electrode is captured in the resin layer, thereby suppressing the migration to a skin. Other resins of this type include carboxylic acid-type resins.

In the case of inorganic ion exchangers, the metal ion dissolved out from the electrode is captured by exchange with a counter ion in the inorganic ion exchanger to prevent the migration to a skin. Examples of such an inorganic ion exchange include synthetic aluminosilicate, anhydrous manganese dioxide, hydrous manganese dioxide, hydrous antimony pentoxide, zirconium phosphate, titanium phosphate, tin (IV) phosphate, zirconium molybdate, zirconium tungstate, cerium (III) oxalate, ammonium molybdate, hexacyanoferrate (III), cobaltate (II) and potassiate, green sand, copper (I) chloride, copper (I) sulfide and the like.

In still another instance using a monovalent metal ion-containing electrode as an anode, a trimethylamine-type quaternary ammonium salt (where the ion consists of chlorine) as an anion exchange resin, and water as a solvent, the reaction on the electrode surface is shown by the following formula (C). Where the metal ion consists of a silver ion, the reaction between the silver and chloride ions is rapid and, thus, takes place in or on the electrode surface or in the vicinity thereof. The silver ion dissolved out from the electrode is converted to silver chloride in or on the surface of the electrode or in the vicinity of the surface, thereby preventing or suppressing the migration to a skin. Other resins of this type include, aside from the quaternary ammonium (dimethylamine type) salts, primary amines, secondary amines, and tertiary amines. The counter ion includes a hydroxyl group or a chloride ion.

$$R-N^+(CH_3)_3Cl^- + Ag^+ \rightarrow R-N(CH_3)_3^+ + AgCl \quad\quad (C)$$

For the formation of the hydrophilic, polymeric gel layer used in the practice of the invention, there is used a material which is able to disperse an ion exchange resin and is also able to dissolve an effective component in the drug layer when the resultant device is used. The hydrophilic, polymeric gel has the function of releasing water therefrom, in which a drug is dissolved, and also has the function of suppressing the reverse diffusion of a once dissolved drug. Such hydrophilic, polymeric gels include polysaccharides, their derivatives, and salts thereof and include, for example, xanthan gum, locust bean gum, carrageenan, gellam gum, tamarind gum, curdlan, pectin, furcellaran, guar gum, alginic acid, sodium alginate, tara gum, karaya gum, cellulose and derivatives thereof. These may be used singly or in combination. If necessary, the gel layer may further comprise electrolytes, pH adjusters, stabilizers, thickeners, wetting agents, surfactants, dissolution aids, absorption promoters, preservatives and the like.

The drug holder or retainer of the iontophoretic device of the invention may be made of various types of members which are capable of retaining a drug therein and which have a porous or capillary structure through which a dissolved drug is permeable (the members having a porous or capillary structure being sometimes referred to simply as a porous member or body in the present specification). A preferred porous body includes an organic one. Examples of the organic porous body include fibrous bodies or masses made of natural fibers such as cellulose, semi-synthetic fibers such as cellulose acetate, and synthetic fibers such as polyethylene, polypropylene, nylons, polyesters and the like, paper sheets, woven or non-woven fabrics, and porous synthetic resins such as porous polypropylene, porous polystyrene, porous polymethyl methacrylate, porous nylons, porous polysulfones, porous fluorine resins, fluorinated polyvinylidene having an introduced hydrophilic group, and the like. Especially, the fluorinated polyvinylidene having an introduced hydrophilic group is preferred because this resin is low in adsorption of a drug, such as a peptide, and is able to readily release on contact with water.

The porous body is not critical with respect to its shape and may be appropriately used in the form of a sheet or the like. When a porous body is in the form of a sheet, its thickness is appropriately selected depending on the amount of a drug to be retained and is, for example, in the range of about 1 to about 500 $\mu$m, preferably about 10 to about 200 $\mu$m. The porous body may be soft or flexible, or may have plasticity, or may be non-deformable. Since the porous body is in direct contact with a skin, the body should preferably be soft and plastic. The area of the sheet-shaped porous body is appropriately selected depending on the amount of a drug to be retained and the area of a skin or mucosa to be contacted. For example, the area is in the range of about 1 to about 100 $cm^2$, preferably from about 1 to about 20 $cm^2$ and more preferably from about 2 to about 10 $cm^2$. The pore size of the sheet-shaped porous body is conveniently selected within a range not impeding the retaining amount and the releasing property of a drug. For example, an average pore size is in the range of about 0.01 to about 50 $\mu$m, preferably from about 0.2 to about 20 $\mu$m.

The drugs retained in the porous body in the practice of the invention include various types of drugs which are ionizable and are transdermally absorbed and include, for example, biologically active peptides or proteins whose molecular weight is about 8000 or less. As for the ionization, it is sufficient that at least a part of a drug being retained is ionized. The ionized drug may be an anionized one or a cationized one. Preferably, cationized drugs are used. Physiologically active peptides include, for example, those peptides shown in (1) to (9) below, of which peptides having a molecular weight of 5000 or less are preferably used.

(1) 1) Luteinizing hormone-releasing hormone (LH-RH), 2) derivatives thereof (herein "derivatives thereof" of proteins and peptides includes their analog, muteins, fractions and the structurally similar peptide which have similar function or activities) having such an activity as LH-RH, and 3) polypeptides represented, for example, by the following formula (I) or salts thereof (U.S. Pat. Nos. 3853837, 4008209 and 3972859, British Patent No. 1423083, and Proceedings of the National Academy of Science, Vol. 78, pp. 6509 to 6512 (1981))

$$(Pyr)Glu-R1-Trp-Ser-R2-R3-R4-Arg-Pro-R5 \quad\quad (I)$$

wherein R1 represents His, Tyr, Trp or p-$NH_2$-Phe, R2 represents Tyr or Phe, R3 represents Gly or a D-amino acid residue, R4 represent Leu, Ile or Nle, and R5 represents Gly-NH-R6 in which R6 represents hydrogen atom or a lower alkyl group which may have a hydroxyl group or NH-R6 in which R6 is as defined above.

(2) 1) LH-RH antagonists, and 2) polypeptides represented, for example, by the following formula (II) or salts thereof (U.S. Pat. Nos. 4086219, 4124577, 4253997 and 4317815)

N-α-butoxycarbonyl-O-benzyl-Ser-Trp-Ser-Tyr-X1-Leu-Arg-Pro-GlyNH$_2$  (II)

wherein X1 represents D-Ser or D-Trp.

(3) 1) Insulin, 2) somatostatin, 3) somatostatin derivatives, and 4) polypeptides represented, for example, by the following formula (III) or salts thereof (U.S. Pat. Nos. 4087390, 4093574, 4100117 and 4253998)

(III)

H—L—Ala—Y—L—Cys—L—Lys—Z—L—Phe—L—Phe—D—Trp—L—Lys—L—

Thr—L—Phe—L—Thr—L—Ser—L—Cys—OH wherein Y represents D-Ala, D-Ser- or D-Val, and Z represents Asn or Ala.

(4) 1) Adrenocorticotropic hormone (ACTH), 2) melanocyte-stimulating hormone (MSH), 3) thyroid stimulating hormone releasing hormone (TRH) and derivatives thereof, and 4) compounds represented, for example, by the following formula (IV) or salts thereof (Japanese Laid-open Patent Application Nos. 50-121273 and 52-116465

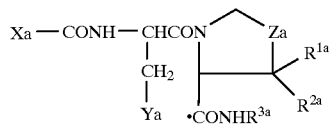

(IV)

wherein Xa represents a 4, 5 or 6-membered heterocyclic group, Ya represents imidazol-4-yl or 4-hydroxyphenyl, Za represents $CH_2$ or S, $R^{1a}$ and $R^{2a}$ may be the same or difference and represent hydrogen atom or a lower alkyl group, and $R^{3a}$ represents hydrogen atom or an optionally substituted aralkyl group.

(5) Parathyroid hormone (PTH) and derivatives thereof including 1) peptides represented, for example, by the following formula (V) or salts thereof (Japanese Laid-open tides of formula (V) or salts thereof, and hPTH (1→34) include bone disease such as osteoporosis, and fractures, myocardial infarction and the like.

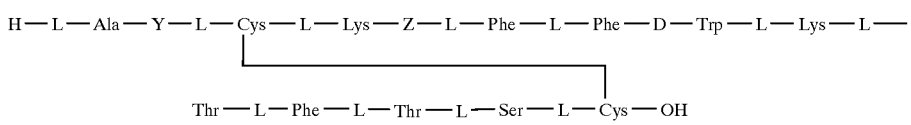

wherein R1' represents Ser or Aib, R2' represents Met or a naturally-occurring lipophilic amino acid, R3' represents Leu, Ser, Lys or an aromatic amino acid, R4' represents Gly or a D-amino acid residue, R5' represents Lys or Leu, R6' represents Met or a naturally occurring fat-soluble amino acid residue, R7' represents Glu or a basic amino acid residue, R8' represents Val or a basic amino acid residue, R9' represents Trp or 2-(1,3-dithiolan-2-yl)Trp, R10' represents Arg or His, R11' represents Lys or His, R12' represents Lys, Gln or Leu, and R13' represents Phe or Phe-NH$_2$.

(6) 1) Oxytocin, 2) calcitonin, 3) derivatives having a function similar to calcitonin, 4) compounds represented, for example, by the following formula (VI) or salts thereof [Endocrinology, 1992, 131/6 (2885–2890)], glucagon, 6) gastrin, 7) secretin, 8) cholecystokinin and 9) angiotensin Cys-Ser-Asn-Leu-Ser-Thr-X$^b$-Val-Leu-Gly-Lys-Leu-Ser-Gln-Glu-Leu-His-Lys-Leu- Gln-Thr-Tyr-Pro-Arg-Thr-Asp-Val-Gly-Ala-Gly-Thr-Pro   (VI)

wherein X$^b$ represents 2-aminosberic acid residue.

(7) 1) Enkephalin, 2) derivatives of enkephalin, and 3) peptides represented, for example, by the following formula (VII), or salts thereof (U.S. Pat. No. 4277394 and European Laid-open Patent Application No. 31567), 4) oligopeptides and endorphins (VII)

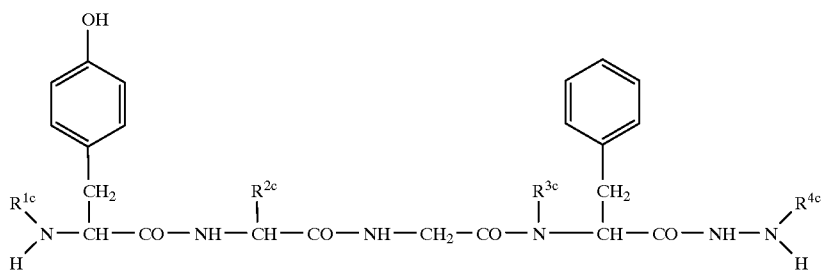

Patent Application Nos. 5-32696 and 4-247034, and European Patent Laid-open Application Nos. 510662, 477885 and 539491), 2) a peptide fragment terminated with N of human PTH (1→34 position) (hereinafter referred to simply as hPTH (1→34)) [G. W. Tregear et al., Endocrinology, 93, 1349–1353 (1973)], and 3) vasopressin and vasopressin derivatives {e.g. desmopressin [Journal of Society of Endocrinology, Japan, Vol. 54, No.5, pp.676–691 (1978)]}. The diseases to be applied through the iontophoretic administration of the above-mentioned PTH and derivatives, pepwherein $R^{1c}$ and $R^{3c}$ independently represent hydrogen atom or an alkyl group having 1 to 6 carbon atoms, $R^{2c}$ represents hydrogen atom or a residue of D-α-amino acid residue, $R^{4c}$ represents hydrogen atom or an optionally substituted aliphatic acyl group having 1 to 8 carbon atoms.

(8) 1) Kyotorphine, 2) interleukins (I to XI), 3) tuftsin, 4) thymopoietin, 5) thymus humoral factor (THF), 6) factor of thymus in serum (FTS) and derivatives thereof, 7) peptides represented by the following formula (VIII), or salts thereof (U.S. Pat. No. 4229438), and 8) other thymus hormones [e.g.

thymocins $\alpha_1$ and $\beta_4$, thymic factor X and the like, "Journal of Clinical Experimental Medicine (Igakuno Ayumi)", Vol. 125, No. 10, pp. 835–843 (1983)]

PGlu-Xd-Lys-Ser-Gln-Yd-Zd-Ser-Asn-OH  (VIII)

wherein Xd represents L-Ala or D-Ala, Yd and Zd independently represent Gly or a D-amino acid residue having 3 to 9 carbon atoms.

(9) a) Motilin, b) dynorphin, c) bombesin, d) neurotensin, e) cerulein, f) bradykinin, g) urokinase, h) substance P, i) polymyxin B, j) colistin, k) gramicidin, l) bacitracin, m) protein synthesis-stimulating peptide, n) gastric inhibitory polypeptide (GIP), o) vasoactive intestinal polypeptide (VIP), p) platelet-derived growth factor (PDGF), and growth hormone-releasing factor (GRF, somatoclinine).

These physiologically active peptides may be human peptides, or peptides derived from other animals such as bovines, swine, chickens, salmon, eel and the like. Further, active derivatives wherein the structures of the peptides are partially modified may also be used. For instance, there may be used insulin derived from swine, calcitonins derived, for example, from swine, chicken, salmon and eel, or a peptide which consists of a human and salmon chimera and represented by the following formula (IX) [Endocrinology, 1992, 131/6, (2885–2890)].

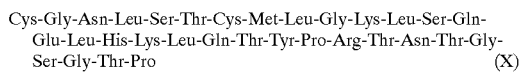
Cys-Gly-Asn-Leu-Ser-Thr-Cys-Met-Leu-Gly-Lys-Leu-Ser-Gln-
Glu-Leu-His-Lys-Leu-Gln-Thr-Tyr-Pro-Arg-Thr-Asn-Thr-Gly-
Ser-Gly-Thr-Pro  (X)

The low molecular weight drugs used in the practice of the invention include compounds whose molecular weight is about 1000 or less and having pharmacological activity. The low molecular weight drugs are not critical with respect to the type and include, for example, antibiotics, antimycotic drugs, hypolipidermic drugs, circulatory drugs, antiplatelet drugs, antitumor drugs, antipyretic, analgesic and/or anti-inflammatory agents, antitussive-expectorant agents, sedatives, muscle relaxtants, antiepileptic drugs, antiulcer drugs, antidepressant agents, antiallergic agents, cordiotoncis, vasodilators, hypotensive-diuretic agents, antiarrhythmic agents, drugs for diabetes, anticoagulants, hemostatic agents, antituberculotic drugs, hormones, narcotic antagonists, bone resorption-inhibitory agents, osteogenetic promoter, angiogenesis inhibitors, and local anaesthetic agents.

Examples of the antibiotic include gentamycin, lividomycin, sisomycin, tetracycline hydrochloride, ampicillin, cefalothin, cefotiam, cefazolin, tienamycin, sulfazecin and the like. Examples of the antimycotic agent include 2-[(1R, 2R)-2-(2,4-difluorophenyl-2-hydroxy-1-methyl-3-(1H-1,2,4-triazol-1-yl)propyl]-4-[4(2,2,3,3-tetrafluoropropoxy)phenyl]-3-(2H, 4H)-1,2,4-triazolone and the like. Examples of the hypolipidermic drugs include paravastatin, simvastatin, and the like. Examples of the circulatory drug include delapril hydrochloride and the like.

Examples of the antiplatelet drug include ticlopidine, cilostazol, limaprostat, aspirin and the like. Examples of the antitumor drug include bleomycin hydrochloride, actinomycin D, mitomycin C, adriamycin, fluorouracil and the like. Examples of the antipyretic, analgesic and/or anti-inflammatory agents include sodium salicylate, sulpyrine, indomethacin sodium, dichlorophenac sodium, buprenorphine hydrochloride, pentazocine, eptazocine hydrobromide, butorphanol tartarate, tramazole hydrochloride, ketrolac, meperidine hydrochloride, morphine hydrochloride, morphine sulfate, hydromorphone (hydromorphine), fentanyl citrate, fentanyl and the like. Examples of the antitussive and expectorant agent include ephedrine hydrochloride, codeine phosphate, picoperidamine hydrochloride. Examples of the sedative include chloropromazine hydrochloride, atropine sulfate and the like. Examples of the local anaesthetic agents include Lidocaine and the like. Examples of the muscle relaxant include pridinol methanesulfonate, tubocurarine chloride and the like. Examples of the antiepileptic agent include phenytoin sodium, ethosuximide, and the like.

Examples of the antiulcer drug include metoclopramide and the like. Examples of the antidepressant include imipramine, phenelzine sulfate and the like. Examples of the antiallergic drug include diphenylhydramine hydrochloride, tripelennamine hydrochloride, clemizole hydrochloride and the like. Examples of the cardiotinic include trans-7r-oxocamphor, theophyllol and the like. Examples of the antiarrhythymic agent include propranolol hydrochloride, oxyprenolol hydrochloride and the like. Examples of the vasodilator include oxyfedrine hydrochloride, tolazoline hydrochloride, bamethan sulfate and the like. Examples of the hypotensive-diuretic agent include pentolinium, hexamethonium bromide and the like. Examples of the antidiabetic agent include glymidime sodium, glypizide, metformin and the like. Examples of the anti-coagulant include sodium citrate and the like.

Moreover, examples of the hemostatic include menadione sodium bisulfite, acetomenaphtone, tranexamic acid and the like. Examples of the antituberculosis drug include isoniazid, ethambutol and the like. Examples of the hormone drug include β-estradiol, testosterone, prednisolone succinate, dexamethasone sodium sulfate, methimazole and the like. Examples of the narcotic antigonist include levalorphan tartarate, nalorphine hydrochloride and the like. Examples of the bone resoption inhibitors include (sulfur-containing alkyl)aminomethylene bisphosphoate. Examples of the angiogenesis inhibitor include a vascularization inhibitory steroid [Science, Vol. 221, p. 719 (1983)], and fumagillol derivatives [e.g. O-monochloroacetyl-carbamoylfumagillol, O-dichloroacetylcarbomoylfumagillol (European Laid-open Patent Application Nos. 357061, 359036, 386667 and 415294)].

These drugs may be retained by dissolving them, for example, in distilled water for injection or physiological saline for injection and applying the resultant solution to the drug-retaining layer according to an ordinarily employed procedure including, for example, impregnation, spraying or dipping and drying. At the time of administration of a drug through iontophoresis, a humectant can suppress the evaporation of water or moisture from the drug solution, permitting an electric current to be applicable to the resultant device over a long time. In addition, the humectant acts on the keratin which serves as a barrier for skin permeation of a drug, so that the transdermal absorption of the drug is promoted in response to an electric current being apwhen no electric current s not absorbed when an electric current is not applied but is absorbed on application of the electric current) without impeding the keratin, thus leading to a high bioavailability of the drug. Thus, when using a drug administration composition for iontophoresis which is characterized by comprising a humectant in the composition, more effective administration is ensured.

The humecant is not critical so long as it can suppress evaporation of moisture or water from a drug solution, keep moisture on the skin surface, the mucosal membrane surface and the drug retainer or holder, and effectively act on the keratin of the skin or the mucosal membrane without adversely influencing the skin or mucosal membrane. Preferably, amines are used. Examples of the amides include urea, dimethylacetamide, diethyltolamide, diethylformamide, dimethyloctamide, dimethyldecamide, biodecomposable urea (1-alkyl-4-imidazolin-2-on), N-methyl-2-pyrrolidone, 2-pyrrolidone, 1-lauryl-2-pyrrolidone, 1-methyl-4-carboxy-2-pyrrolidone, 1-hexyl-4-methoxycarbonyl-4-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-coco alkyl-pyrrolidone, N-tallowalkylpyrrolidone, N-(2-hydroxyethyl)-2-pyrrolidone, 1-dodecylazacycloheptan-2-on, 1-geranylazacycloheptan-2-on, 1-farnesylazacycloheptan-2-on, 1-(3,7-dimethyloctyl)azacycloheptan-2-on, 1-(3,7,11-trimethyldodecyl)azacycloheptan-2-on, 1-geranylazacyclohexan-2-on, 1-geranylazacyclopentan-2,5-dion, 1-farnesylazacyclopentan-2-on, 1-[2-(decylthio)ethyl]azacyclopentan-2-on, and the like. Of these, urea and N-methyl-2-pyrrolidone are preferred. The use of urea and N-methyl-2-pyrrolidone in combination is more effective.

In order to further reduce the skin stimulation at the time of the iontophoretic administration, it is effective to use amino acids or derivatives as an additional humectant in the form of mixtures with the amides. Such additional humectants include polyhydric alcohols, sugar alcohols, acidic mucopolysaccharides and amino acids (including amino acid derivatives and cyclic amino acids). Of these, the amino acids, amino acid derivatives and cyclic amino acids are preferably used although it is not critical with respect to the types thereof and include, for example, glycine, alanine, valine, leucine, isoleucine, serine, threonine, glutamic acid, aspartic acid, phenylalanine, tyrosine, tryptophane, proline, hydroxyproline, alginine, lysine, histidine, L-$\alpha$-aminobutyric acid L-methylglutamic acid, $\alpha$-methyl-D-serine, pyrrolidonecaboxylic acid, piperidyl carbonyl, piperidyl methylcarbonyl, pyrrolidinyl carbonyl (prolyl), pyrrolidnyl methylcarbonyl and the like. Most preferably, L-proline is used. The drug in a drug administration composition comprising these humectants should preferably be applied in the form of a preparation cationized with a buffer solution. Preferably, the buffer solution is one which contains a water-soluble aliphatic carboxylic acid having 2 to 6 carbon atoms such as citric acid, its salt and/or hydrate.

Where the drug used is a biologically active peptide, disaccharides such as, for example, trehalose, maltose, mannitol, inositol and the like may be added to the drug solution in an amount, for example, of about 1 to about 100 mg/ml. The addition of disacchrides contributes to increasing the stability of the drug in a dry condition. When the drug-retaining layer is preserved in a dry condition, the drug retained in the layer can be preserved over a long time while keeping its activity. More particularly, after the drug-retaining layer containing a drug has been well dried, this layer is packed, according to a method such as a vacuum seal packaging, in a film (e.g. an aluminium foil or film) whose moisture permeability is very low. In order to ensure the dry conditions, a drying agent [e.g. a zeolite drying agent such as Ceramu (trademark) (Registered Trade Name of Toikai Chemical Co., Ltd.) or a silica gel drying agent] may be incorporated in the package when the vacuum seal packaging is performed. If a drug undergoes oxidative decomposition, an oxygen absorbing agent [e.g. Ageless (Registered Trade Name of Mitsubishi Gas Chemical Co., Ltd.)] may further be incorporated along with the drying agent.

The drug should be present in the drug-retaining layer in an effective amount which depends on the type of drug, the type of drug-retaining layer and the site of administration. For instance, the amount is in the range of from about 0.1 to about 50000 $\mu$g, preferably from about 0.5 to about 1000 $\mu$g/cm$^2$ of the drug-retaining layer. The liquid for dissolving a drug may contain an appropriate type of adsorption inhibitor for inhibiting the loss by adsorption of biologically active peptides and proteins due to adsorption [e.g. bovine serum albumin (BSA), human serum albumin, benzalkonium chloride, benzethonium chloride, Tween 80 and the like].

The invention is more particularly described by way of experimental examples using the iontophoresis of the dissolution-on-use type, which should not be construed as limiting the invention thereto. In Experimental Example 1, human parathyroid hormone [hPTH (1→34)] was used to check the effect of ion exchange resins on the inhibition of ions from being dissolved out from an electrode and the absorption of a drug. In Experimental Example 2, the influence of ion exchange resins on the drug absorption was checked by use of salmon calcitonin (sCT). In Experimental Example 3, the effect of ion exchange resins on the inhibition of ions from being dissolved out from an electrode and the absorption of a drug. In experimental examples, the contents of all components are by weight.

EXPERIMENTAL EXAMPLE 1

This Experimental Example 1 was conducted using the device shown in FIGS. 1 and 2. The materials and sizes of the individual members of the device were, respectively, those which were particularly described with reference to FIGS. 1 and 2 hereinbefore. Male SD rats (seven weeks old) were clipped with a hair clipper at an abdominal skin area thereof and then treated with a shaver under anesthetization with pentobarbital, followed by slightly rubbing with an absorbent cotton containing a 70% aqueous solution of ethanol for the purpose of defatting and disinfection. An applicator for a drug was attached to the abdominal skin of the rat, and a 12% PVA gel (containing a polyvinyl alcohol gel and 0.9% of sodium chloride and having a thickness of 2 mm) was used as a reference electrode (cathode). A silver electrode was fixed to the applicator, and a silver chloride electrode (2.5 cm$^2$) was fixed as the reference electrode (cathode).

In the iontophoresis, a pulse depolarization direct current (frequency=30 kHz, on/off=3/7, and voltage=10 V) caused by a short-circuiting switch was used, and the current was applied to for 45 minutes in total (wherein a cycle of applying the electric current for 15 minutes and stopping the current application for 5 minutes was repeated three times). The concentration of hPTH (1→34) in serum was determined according to the radioimmunoassay method using Rat PTH Kit (Nicols Co., Ltd.). The experiment was conducted in such a way that 40 $\mu$g of hPTH (1→34) used a drug was contained in the drug retaining membrane 8. The contents of all components are by weight. The hydrophilic, polymeric gel layers 4 of FIG. 1 were, respectively, made of the compositional liquids indicated in the respective examples and comparative examples. Table 1 shows ion exchange resins used in Examples 1 to 7.

TABLE 1

|  | Type of Resin | Name of Resin | Polymeric Backbone | Functional Group | Counter Ion |
|---|---|---|---|---|---|
| Example 1 | chelate resin | Amberlite JRC-718 | styrene polymer | —N=(CH$_2$COO)$_2$M | Na$^+$ |
| Example 2 | cation exchange resin (strongly acidic) | IRC-120B | styrene polymer | —SO$_3$M | Na$^+$ |
| Example 3 | cation exchange resin (weakly acidic) | CG-50 | methacrylic polymer | —COOM | H$^+$ |
| Example 4 | anion exchange resin (strongly basic) | IRA-400 (I) | styrene polymer | —NM≡(CH$_3$)$_3$ | Cl$^-$ |
| Example 5 | anion exchange resin (strongly basic) | IRA-410 (II) | styrene polymer | —NM(C$_2$H$_4$OH)=(CH$_3$)$_2$ | Cl$^-$ |
| Example 6 | anion exchange resin (moderately basic) | IRA-68 | acrylic polymer | —N(CH$_3$)$_2$ | OH$^-$ |
| Example 7 | anion exchange resin (weakly basic) | IRA-93ZU | styrene polymer | —N(CH$_3$)$_2$ | OH$^-$, Cl$^-$ |

| Components | Content (%) |
|---|---|
| Example 1 | |
| Agar | 1 |
| Amberlite IRC-718 (Organo Co., Ltd.) | 50 |
| Distilled water for injection | 49 |
| Total | 100 |
| Example 2 | |
| Agar | 1 |
| Amberlite IR-120B (Organo Co., Ltd.) | 50 |
| Distilled water for injection | 49 |
| Total | 100 |
| Example 3 | |
| Agar | 1 |
| Amberlite CG-50 (Organo Co., Ltd.) | 50 |
| Distilled water for injection | 49 |
| Total | 100 |
| Example 4 | |
| Agar | 1 |
| Amberlite IRA-400 (Organo Co., Ltd.) | 50 |
| Distilled water for injection | 49 |
| Total | 100 |
| Example 5 | |
| Agar | 1 |
| Amberlite IRA-410 (Organo Co., Ltd.) | 50 |
| Distilled water for injection | 49 |
| Total | 100 |
| Example 6 | |
| Agar | 1 |
| Amberlite IRA-68 (Organo Co., Ltd.) | 50 |
| Distilled water for injection | 49 |
| Total | 100 |
| Example 7 | |
| Agar | 1 |
| Amberlite IRA-93ZU (Organo Co., Ltd.) | 50 |
| Distilled water for injection | 49 |
| Total | 100 |
| Comparative Example 1 | |
| Agar | 1 |
| Distilled water for injection | 99 |
| Total | 100 |

TABLE 1-continued

Comparative Example 2

| | |
|---|---|
| Agar | 1 |
| Sodium chloride | 3 |
| Distilled water for injection | 96 |
| Total | 100 |

Figure 3:
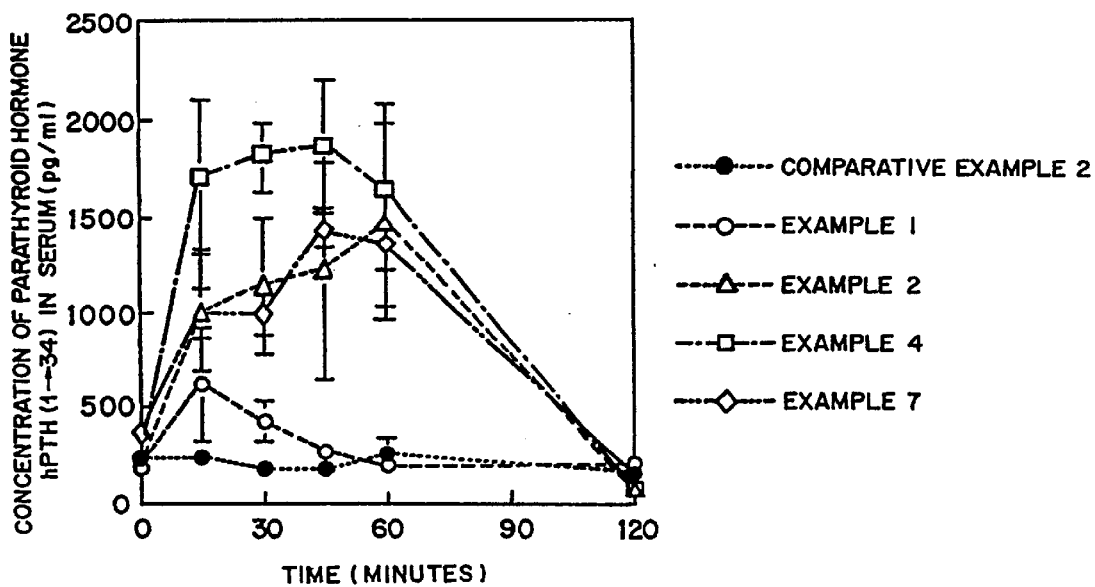
FIG. 3 is a graph showing the concentration of hPTH (1→34) in serum in relation to the variation in time for Examples 1, 2, 4 and 7 and also for Comparative Example 2.

The results obtained in Examples 1 to 7 and Comparative Examples 1, 2 are shown in FIG. 3 and Table 2.

More particularly, FIG. 3 shows the results of Example 1 (indicated by symbol "○" in FIG. 3), Example 2 (indicated by symbol "Δ" in FIG. 3), Example 4 (indicated by symbol "□" in FIG. 3), Example 7 (indicated by symbol "◇" in FIG. 3), and Comparative Example 2 (indicated by symbol "●" in FIG. 3). As will be apparent from FIG. 3, a higher peptide concentration in serum is more reproducibly obtained in Examples 1, 2, 4 and 7 than in Comparative Example 2. Especially, with Examples 2, 4 and 7, much better results are obtained. The bioavailability (B. A.) which was calculated from an area under peptide-in-serum concentration-time curve (AUC) obtained by intravenous administration of hPTH (1→34) at a dose of 2 μg/kg is as shown in Table 2. As shown in Table 2, since the ion exchange resins are used in Examples 1 to 7, no silver ion was deposited on the skin as would be observed in Comparative Example 1 and the bioavailabilites were higher.

TABLE 2

| Example | Deposition of Silver Ion on Skin | B.A. ± SE |
|---|---|---|
| Comparative Example 1 | yes | 2.70 ± 0.13 |
| Comparative Example 2 | no | 0.11 ± 0.04 |
| Example 1 | no | 3.29 ± 0.76 |
| Example 2 | no | 4.83 ± 2.07 |
| Example 3 | no | 2.68 ± 0.79 |
| Example 4 | no | 7.32 ± 1.58 |
| Example 5 | no | 4.30 ± 0.18 |
| Example 6 | no | 0.76 ± 0.20 |
| Example 7 | no | 4.08 ± 1.28 |

The bioavailability (B. A.) was calculated from the intravenous administration (2 μg/kg).

EXPERIMENT 2

In Experiment 2, the experimental procedure was conducted substantially in the same manner as in Experiment 1 wherein an applicator used was as shown in FIGS. 1, 2. The constituent materials and sizes of the respective members were those particularly described hereinbefore with reference to FIGS. 1, 2. The drug used in the experiment was 10 international units (2 μg) of sCT (Nova Co., Ltd.) contained in the drug retaining membrane (Biodyne membrane of Paul Co., Ltd.). The ion exchange resin used was a strongly basic anion exchange resin, i.e. cholestyramine, (a quaternary ammonium salt containing a chloride ion, made by Sigma Co., Ltd.). For the iontophoresis, a pulse depolarization direct current (frequency=30 kHz, on/off=3/7 and voltage=10V) caused by a short-circuiting switch was used, and the electric current was continuously applied to for 45 minutes. The sCT concentration in serum was determined according to a radioimmunoassay method using sCT kit (Penensula Laboratories Co., Ltd.).

| Components | Content (%) |
|---|---|
| Example 8 | |
| Agar | 1 |
| Cholestyramine | 5 |
| Distilled water for injection | 94 |
| Total | 100 |
| Comparative Example 3 | |
| Agar | 1 |
| Distilled water for injection | 99 |
| Total | 100 |

Figure 4:
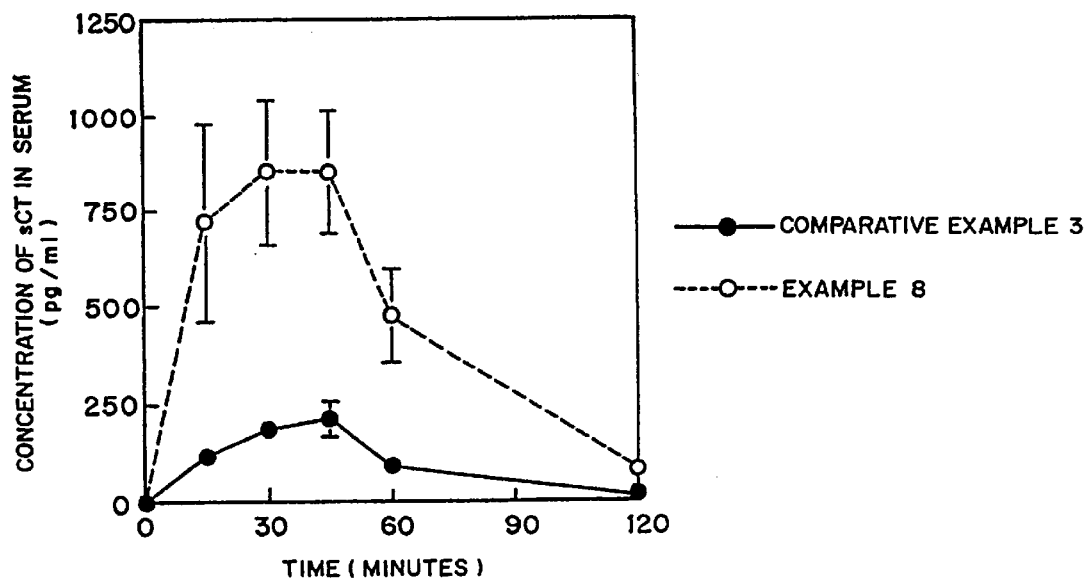
FIG. 4 is a graph showing the concentration of sCT in serum in relation to the variation in time for Example 8 and Comparative Example 3.

The results obtained in Example 8 and Comparative Example 3 are shown in FIG. 4 and Table 3. FIG. 4 reveals that in Example 8, a higher peptidein-serum concentration could be more reproducibly obtained than in Comparative Example 3. The bioavailability which was calculated from an area under peptide-in-serum concentration-time curve (AUC) obtained by intravenous administration of sCT at a dose of 2 μg/kg is as shown in Table 3. As will be apparent from table 3, since the ion exchange resin was used in Example 8, no deposition of the silver ion was observed and the bioavailability was much higher than in Comparative Example 3.

TABLE 3

| Example | Deposition of Silver ion on Skin | B.A. (average value ± standard error) |
|---|---|---|
| Comparative Example 3 | yes | 2.20 ± 0.26 |
| Example 8 | no | 11.14 ± 3.12 |

EXPERIMENTAL EXAMPLE 3

In Experimental Example 3, the device used was as shown in FIGS. 1 and 2 and the experimental procedure was conducted substantially in the same manner as in Experiment 1. The constituent materials and sizes of the respective members were those particularly described hereinbefore with reference to FIGS. 1 and 2. In the device of the type shown in FIGS. 1 and 2, the compositional liquids indicated in the respective examples were applied to an agar gel layer 4 as a liquid electric conductor. 40 μg of hPTH (1→34) was contained in the drug retaining membrane 8 as a drug. The contents of individual components are by weight.

| Components | Content (%) |
|---|---|
| Example 9 | |
| Urea | 5 |
| Agar | 1 |

-continued

| Components | Content (%) |
|---|---|
| Cholestyramine | 8 |
| Citric acid monohydrate | 0.25 |
| Trisodium citrate dihydrate | 0.7 |
| Distilled water for injection | 85.05 |
| Total | 100 |

Example 10

| Components | Content (%) |
|---|---|
| N-Methyl-2-pyrrolidone | 5 |
| Agar | 1 |
| Cholestyramine | 8 |
| Citric acid monohydrate | 0.25 |
| Trisodium citrate dihydrate | 0.7 |
| Distilled water for injection | 85.05 |
| Total | 100 |

Example 11

| Components | Content (%) |
|---|---|
| Urea | 5 |
| N-Methyl-2-pyrrolidone | 5 |
| Agar | 1 |
| Cholestyramine | 8 |
| Citric acid monohydrate | 0.25 |
| Trisodium citrate dihydrate | 0.7 |
| Distilled water for injection | 80.05 |
| Total | 100 |

Figure 5:
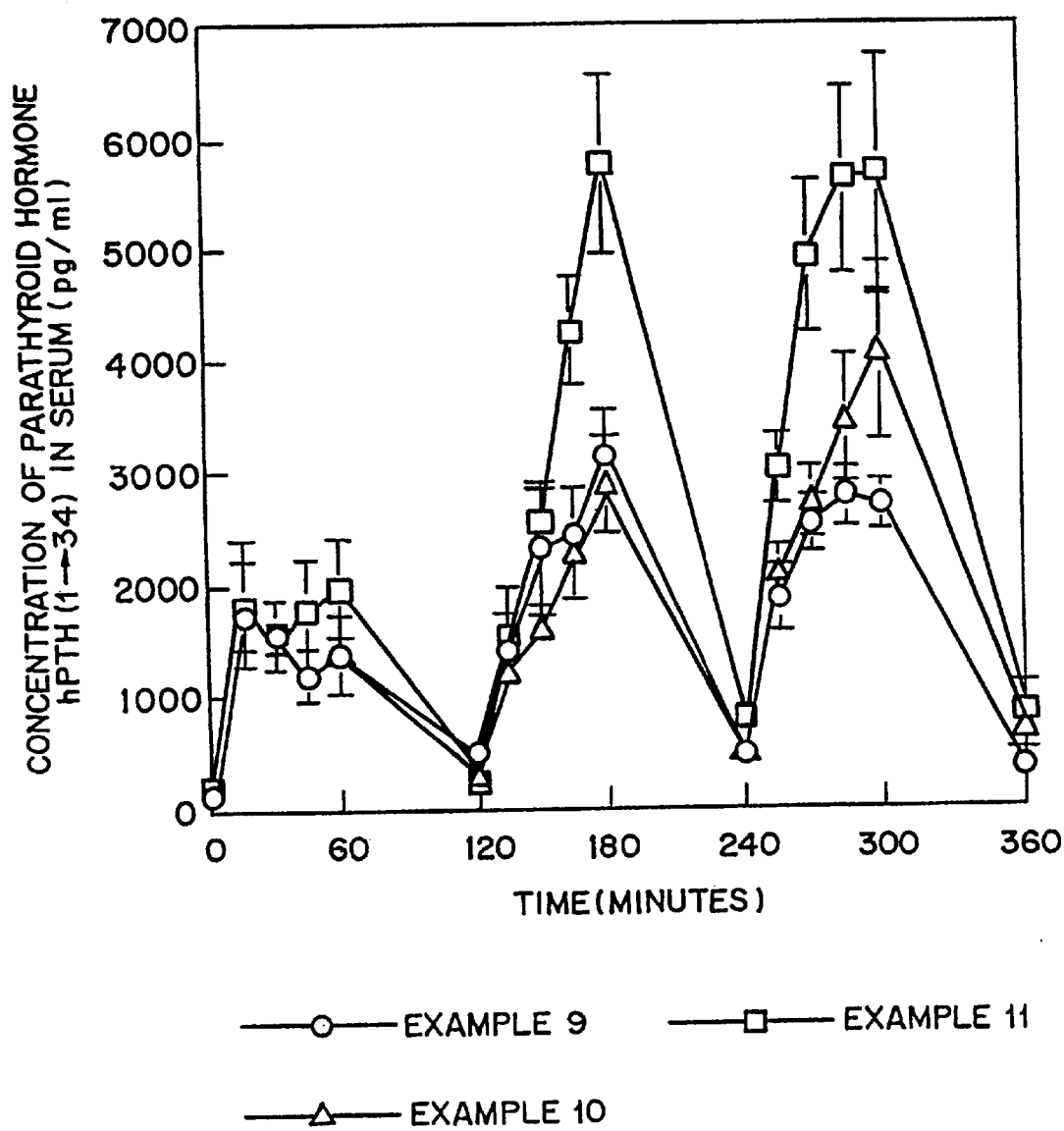
FIG. 5 is a graph showing the concentration of hPTH (1→34) in serum in relation to the variation in time for Examples 9 to 11.

FIG. 5 and Table 4 show the results obtained in Examples 9 to 11. As will be apparent from FIG. 5, a high peptide concentration in serum can be reproducibly obtained in Example 9 (indicated by symbol "○" in FIG. 5), Example 10 (indicated by symbol "Δ" in FIG. 5), and Example 11 (indicated by symbol "□" in FIG. 5), respectively. Especially, with Example 11 (indicated by symbol "□" in FIG. 5), urea and N-methyl-2-pyrrolidone are used in combination as a humectant, which is better than the cases of Example 9 (using urea alone and indicated by symbol "○" in FIG. 5) and Example 10 (using N-methyl-2-pyrrolidone alone and indicated by symbol "Δ" in FIG. 5). With Example 11, the concentration of the parathyroid hormone hPTH (1→34) in serum arrived at about 5900 pg/ml at the second cycle and 5700 pg/ml at the third cycle. Table 4 shows the bioavailabilities (B.A.) calculated from an area under peptide-in-serum concentration-time curve (AUC) which was determined by the intravenous administration of 2 μg/kg of hPTH (1→34). This table reveals that the bioavailabilites are very high for Examples 9 to 11. Especially, the bioavailability (B.A.) of Example 11 reaches a level as high as 54.85%. In all the Examples 9 to 11, the deposition of any silver ion from the electrode on the skin was not observed.

TABLE 4

| | Bioavailability B.A. % | Standard Error (SE) |
|---|---|---|
| Example 9 | 32.17 | 3.56 |
| Example 10 | 35.72 | 4.31 |
| Example 11 | 54.85 | 5.89 |

EXPERIMENTAL EXAMPLE 4

In Experimental Example 4, the device used was as shown in FIGS. 1 and 2, and the experimental procedure was conducted substantially in the same manner as in Experiment 1. The constituent materials and sizes of the respective members were those particularly described hereinbefore with reference to FIGS. 1 and 2. The iontophoresis was conducted using a pulse depolarization direct current (frequency=50 kHz, on/off=5/5, and electric current=0.7 mA) caused by a short-circuiting switch, wherein the electric current was applied to for 60 minutes. In the device of the type shown in FIGS. 1 and 2, the compositions of the respective examples were each used as a liquid electric conductor for the agar gel layer 4. 200 μg of hPTH (1→34) was impregnated in the drug-retaining membrane 8 as a drug. The contents of individual components are by weight.

| Components | Content (%) |
|---|---|
| Comparative Example 4 | |
| Agar | 1.0 |
| Xanthan gum | 0.25 |
| Locust bean gum | 0.25 |
| Cholestyramine | 5.0 |
| Benzoic acid | 0.2 |
| Methyl benzoate | 0.2 |
| Citric acid monohydrate | 0.25 |
| Trisodium citrate dihydrate | 0.7 |
| Distilled water for injection | 92.15 |
| Total | 100 |

Example 12

| Components | Content (%) |
|---|---|
| Urea | 5.0 |
| Agar | 1.0 |
| Xanthan gum | 0.25 |
| Locust bean gum | 0.25 |
| Cholestyramine | 5.0 |
| Benzoic acid | 0.2 |
| Methyl benzoate | 0.2 |
| Citric acid monohydrate | 0.25 |
| Trisodium citrate dihydrate | 0.7 |
| Distilled water for injection | 87.15 |
| Total | 100 |

Example 13

| Components | Content (%) |
|---|---|
| L-Proline | 10.0 |
| Agar | 1.0 |
| Xanthan gum | 0.25 |
| Locust bean gum | 0.25 |
| Cholestyramine | 5.0 |
| benzoic acid | 0.2 |
| Methyl benzoate | 0.2 |
| Citric acid monohydrate | 0.25 |
| Trisodium citrate dihydrate | 0.7 |
| Distilled water for injection | 82.15 |
| Total | 100 |

Example 14

| Components | Content (%) |
|---|---|
| Urea | 5.0 |
| L-Proline | 10.0 |
| Agar | 1.0 |
| Xanthan gum | 0.25 |
| Locust bean gum | 0.25 |
| Cholestyramine | 5.0 |
| Benzoic acid | 0.2 |
| Methyl benzoate | 0.2 |
| Citric acid monohydrate | 0.25 |
| Trisodium citrate dihydrate | 0.7 |
| Distilled water for injection | 77.15 |
| Total | 100 |

Figure 6:
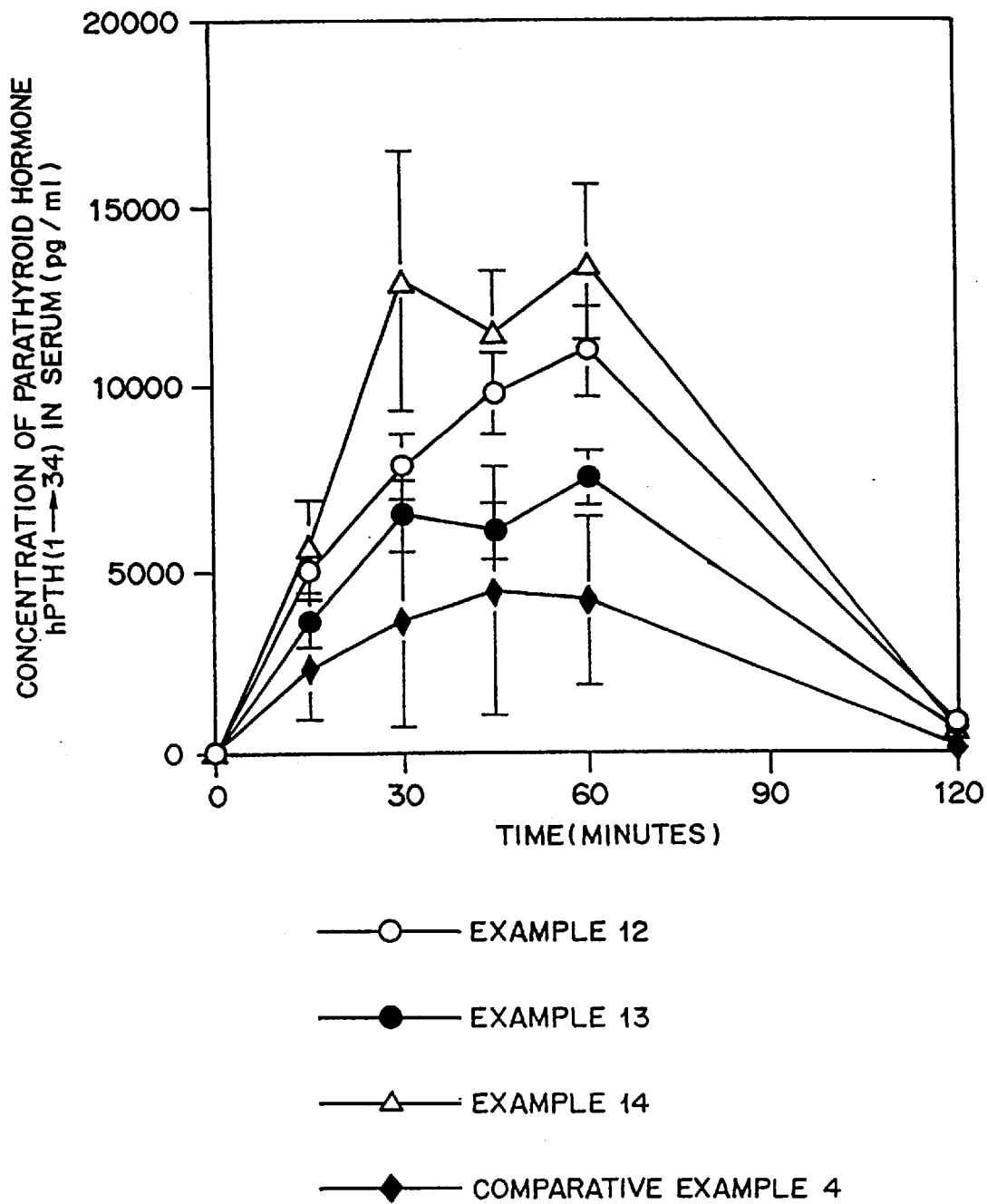
FIG. 6 is a graph showing the concentration of hPTH (1→34) in serum in relation to the variation in time for Examples 12 to 14 and Comparative Example 4.

FIG. 6 and Table 5 show the results obtained in Comparative Example 4 and Examples 12 to 14. As will be apparent from FIG. 6, the peptide concentration in serum was much higher in Example 12 (indicated by symbol "○" in FIG. 6), Example 13 (indicated by symbol "●" in FIG. 6) and Example 14 (indicated by symbol "Δ" in FIG. 6) than in Comparative Example 4 (indicated by symbol "◆" in FIG. 6). In Example 14 (indicated by symbol "Δ" in FIG. 6), urea and L-proline were used in combination as a humectant, which was higher in absorptivity than in the cases of Example 12 (indicated by symbol "○" in FIG. 6) and Example 13 (indicated by symbol "●" in FIG. 6).

Table 5 shows the bioavailabilies (B.A.) calculated from an area under peptide-in-serum concentration-time curve (AUC) which was determined by the intravenous administration of 2 μg/kg of hPTH (1→34). Table 5 reveals that the bioavailabilites are very high for Examples 12 to 14. Especially, in Example 14, a high bioavailability could be obtained under the conditions of this experiment (constant current=0.7 mA).

TABLE 5

|  | Bioavailability B.A. % | Standard Error (SE) |
|---|---|---|
| Comparative Example 4 | 3.21 | 2.06 |
| Example 12 | 8.16 | 0.91 |
| Example 13 | 5.59 | 0.61 |
| Example 14 | 10.16 | 1.85 |

As will be apparent from the foregoing examples, the iontophoretic device structure of the dissolution-on-use type according to the invention can specifically interrupt metal ions dissolved out from a non-polarizable electrode and can prevent the reverse diffusion of a drug solution when a drug is administered according to the iontophoresis of unstable drugs in the form of a solution. Moreover, the device structure keeps the capability of applying an electric current thereto or the electric conductivity over a long time without lowering the transport number of a drug. Using the device structure, the deposition of any electrode component on a skin was completely suppressed, with a high bioavailability of a drug being attained. The device structure is good from the standpoint of economy and productivity.

When a humectant is contained in the hydrophilic, polymeric gel layer and/or the drug layer, the evaporation of moisture or water from a drug solution can be suppressed at the time of administration of the drug, ensuring a long-lasting electric conductivity imparted to the device. The humectant acts on keratin which serves as a barrier for skin permeation of a drug and can thus promote the transdermal or transmucosal absorption of a drug in response to an electric stimulation. This eventually leads to a further improved bioavailability of the drug.

What is claimed is:

1. An iontophoretic device structure of the dissolution-on-use type wherein an ionized drug is transdermally or transmucosally administered into a living body, the device structure comprising (a) a non-polarizable electrode, (b) a hydrophilic, polymeric gel layer having an ion exchange resin dispersed therein which is capable of specifically inhibiting the movement of ions dissolved out from the electrode, and (c) a drug layer containing a drug in a dry condition in a drug retaining membrane, wherein, said drug layer is adapted to be brought into contact with said hydrophilic, polymeric gel layer during use of said device so that said drug in the dry condition is dissolved.

2. The iontophoretic device structure according to claim 1, wherein said non-polarizable electrode is used as an anode and said ionized drug consists of a cationized drug.

3. The iontophoretic device structure according to claim 2, wherein said non-polarizable electrode used as an anode consists of a member selected from the group consisting of silver and a mixture containing silver.

4. The iontophoretic device structure according to claim 2, wherein said cationized drug is at least one member selected from the group consisting of biologically active peptides, biologically active peptide derivatives and salts thereof.

5. The iontophoretic device structure according to claim 1, wherein said hydrophilic, polymeric gel layer comprises at least one member selected from the group consisting of polysaccharides, polysaccharide derivatives and salts thereof.

6. The iontophoretic device structure according to claim 1, wherein said ion exchange resin contained in said hydrophilic, polymeric gel layer consists of an anion exchange resin.

7. The iontophoretic device structure according to claim 6, wherein said anion exchange resin has a quaternary ammonium functional group and a chloride ion.

8. The iontophoretic device structure according to claim 1, wherein said drug retaining membrane of said drug layer comprises a member having a porous or capillary structure.

9. An iontophoretic device structure of the dissolution-on-use type wherein an ionized drug is transdermally or transmucosally administered into a living body, said device structure comprising (a) a non-polarizable electrode, (b) a hydrophilic, polymeric gel layer having an ion exchange resin dispersed therein which is capable of specifically inhibiting the movement of ions dissolved out from the electrode, (c) a drug layer containing a drug in a dry condition in a drug retaining membrane, and (d) a humectant contained in said hydrophilic, polymeric gel layer and/or said drug retaining membrane wherein said drug layer is adapted to be brought into contact with said hydrophilic, polymeric gel layer during use of said device so that said drug in the dry condition is dissolved.

10. The iontophoretic device structure according to claim 9, wherein said humectant consists of an amide.

11. The iontophoretic device structure according to claim 9, wherein said humectant consists of a mixture of at least one amide and at least one member selected from the group consisting of amino acids and derivatives thereof.

12. The iontophoretic device structure according to claim 10, wherein said amide is a member selected from the group consisting of urea, N-methyl-2-pyrrolidone and mixtures thereof.

13. The iontophoretic device structure according to claim 11, wherein said amino acid or derivative thereof consists of a cyclic amino acid.

14. The iontophoretic device structure according to claim 13, wherein said amino acid or derivative thereof consists of L-proline.

15. The iontophoretic device structure according to claim 9, wherein said non-polarizable electrode is used as an anode and said ionized drug consists of a cationized drug.

16. The iontophoretic device structure according to claim 15, wherein said non-polarizable electrode used as an anode consists of a member selected from the group consisting of silver and a mixture containing silver.

17. The iontophoretic device structure according to claim 15, wherein said cationized drug is at least one member selected from the group consisting of biologically active peptides, biologically active peptide derivatives and salts thereof.

18. The iontophoretic device structure according to claim 9, wherein said hydrophilic, polymeric gel layer comprises at least one member selected from the group consisting of polysaccharides, polysaccharide derivatives and salts thereof.

19. The iontophoretic device structure according to claim 9, wherein said ion exchange resin contained in said hydrophilic, polymeric gel layer consists of an anion exchange resin.

20. The iontophoretic device structure according to claim 19, wherein said anion exchange resin has a quaternary ammonium functional group and a chloride ion.

21. The iontophoretic device structure according to claim 9, wherein said drug retaining membrane of said drug layer comprises a member having porous or capillary structure.

22. The iontophoretic device structure according to claim 11, wherein said amide is a member selected from the group consisting of urea, N-methyl-2-pyrrolidone and mixtures thereof.

23. The iontophoretic device structure according to claim 1, wherein said ion exchange resin is selected from the group consisting of a resin having a polystyrene backbone, $-N\!=\!(CH_2COO)_2M$ functional group and $Na^+$ counter ion; a polystyrene backbone, $-SO_3M$ functional group and $Na^+$ counter ion; a polymethacrylic backbone, $-COOM$ functional group and $H^+$ counter ion; a polystyrene backbone, $-NM\!\equiv\!(CH_3)_3$ functional group and $Cl^-$ counter ion; a polystyrene backbone, $-NM(CH_2H_4OH)\!\equiv\!(CH_3)_2$ functional group and $Cl^-$ counter ion; a polyacrylic backbone, $-N(CH_3)_2$ functional group and $OH^-$ counter ion; and a polystyrene backbone, $-N(CH_3)_2$ functional group and $OH^-$ and $Cl^-$ counter ions.

24. The iontophoretic device structure according to claim 1, wherein said ion exchange resin contains a quaternary ammonium salt and a chloride ion.

25. The iontophoretic device structure according to claim 1, wherein said ion exchange resin comprises an iminodiacetic acid resin.

26. The iontophoretic device structure according to claim 1, wherein said ion exchange resin comprises a resin selected from the group consisting of a polyamine resin, a phosphoric acid resin, an amino phosphoric acid resin, a thiol resin, a dithiocarbamic acid resin, an amidoxime resin and a glucamine resin.

27. The iontophoretic device structure according to claim 1, wherein said ion exchange resin contains a member selected from the group consisting of aluminosilicate, manganese dioxide, antimony pentoxide, zirconium phosphate, titanium phosphate, tin (IV) phosphate, zirconium molybdate, zirconium tungstate, cerium (III) oxalate, ammonium molybdate, cobalt hexacyanoferrate (III), potassium hexacyanoferrate (III), copper (I) chloride and copper (I) sulfide.

28. The iontophoretic device structure according to claim 1, additionally comprising (d) a self-adhesive layer for securing the device structure to the living body.

29. The iontophoretic device structure according to claim 9, additionally comprising (e) a self-adhesive layer for securing the device structure to the living body.

* * * * *